Figure 1:
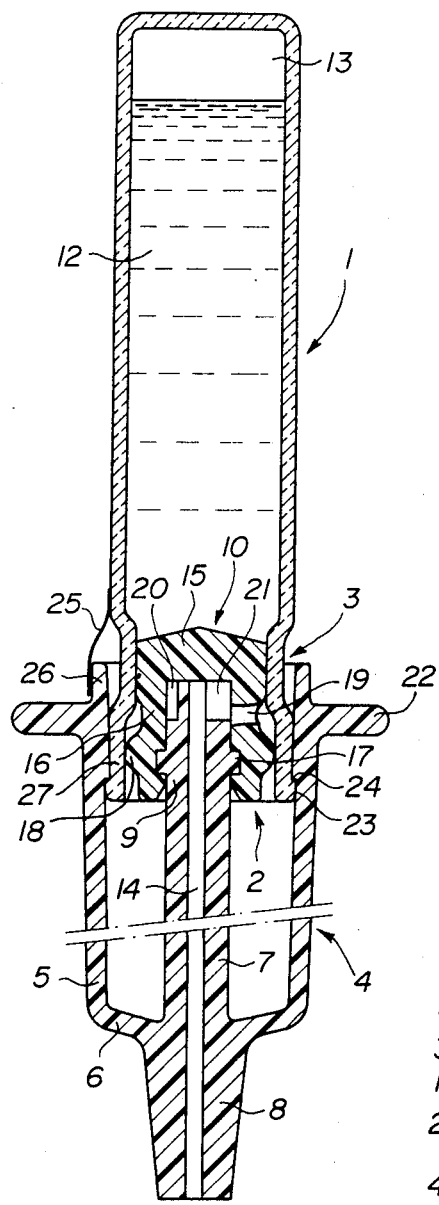

United States Patent [19]

Meyer et al.

[11] Patent Number: 4,610,669
[45] Date of Patent: Sep. 9, 1986

[54] PREFILLED AMPOULE-SYRINGE OF UNITARY DOSE

[75] Inventors: Gabriel Meyer; Ernst Howald, both of Vesenaz, Switzerland

[73] Assignee: Meditec S.A., Luxembourg, Luxembourg

[21] Appl. No.: 691,755

[22] Filed: Jan. 15, 1985

[30] Foreign Application Priority Data

Jan. 25, 1984 [CH] Switzerland ............................ 344/84

[51] Int. Cl.[4] ............................................ A61M 5/315
[52] U.S. Cl. ..................................... 604/218; 604/236
[58] Field of Search .............. 604/218, 238, 236, 240, 604/241, 231, 89, 90, 91; 128/766

[56] References Cited

U.S. PATENT DOCUMENTS

| | | | |
|---|---|---|---|
| 2,893,390 | 7/1959 | Lockhart | 604/238 |
| 3,159,159 | 12/1964 | Cohen | 128/766 |
| 3,161,195 | 12/1964 | Taylor et al. | 604/89 |
| 3,330,280 | 7/1967 | Ogle | 604/89 |

Primary Examiner—John D. Yasko
Attorney, Agent, or Firm—Frost & Jacobs

[57] ABSTRACT

A prefilled ampoule-syringe of unitary dose comprises an ampoule being closed at one of its ends, the other end being open. The ampoule further comprises a narrowed zone. A hollow capsule is arranged at top of the opening of the ampoule. This capsule is connected to a movable stopper means comprising a stopper head and a hollow cylindrical member having a radial channel and a peripheral rim. This rim acts as a retention member during the storage and as a piston ring during the injection. In order to avoid the loss of its elasticity, the rim is located within a belt of enlarged diameter downstream from the narrowed zone during the storage.

10 Claims, 7 Drawing Figures

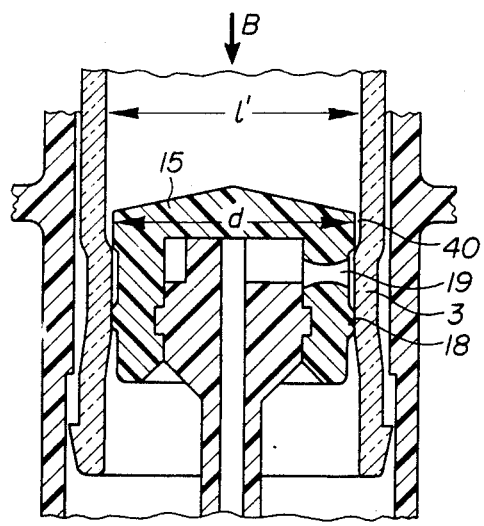
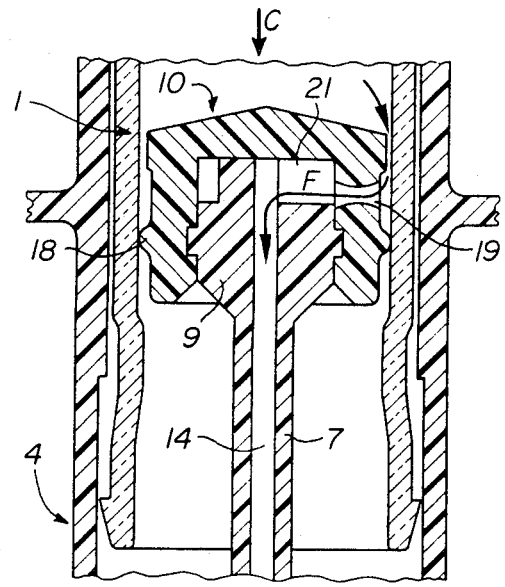
FIG. 4                FIG. 5
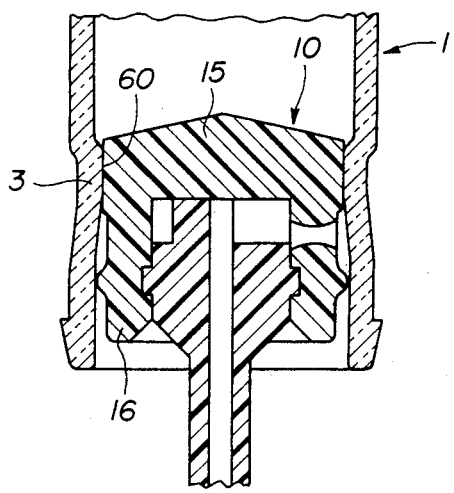
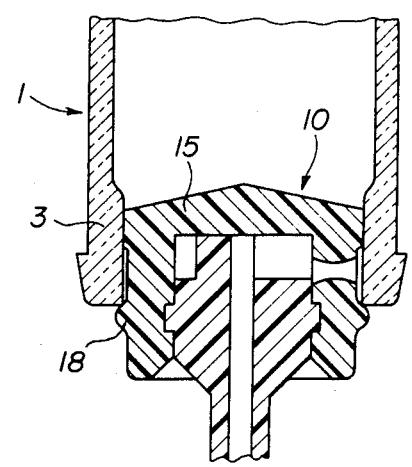
FIG. 6                FIG. 7

PREFILLED AMPOULE-SYRINGE OF UNITARY DOSE

The present invention concerns a prefilled ampoule-syringe of unitary dose comprising an ampoule being open at one of its ends and provided with a narrowed zone near said end, stopper means of elastomeric material being engaged within the ampoule and axially movable between a storage position and a working position, the stopper means comprising an interior conduit provided for bringing into communication a needle holding tip and the interior of the ampoule when the stopper means is in its working position, the interior conduit comprising an axial channel and a radial channel connected to the axial channel, the stopper means being integral with a capsule arranged above the zone of the open end of the ampoule and comprising a stopper head which is prolonged by a flexible hollow cylindrical member which covers a central stiffening tip connecting the stopper means and the capsule, the hollow cylindrical member comprising the radial channel and at least one peripheral rim provided downstream from the radial channel.

The pharmaceutical industries provide through their good fabrication practices and serious controls medicaments of very high quality. However too often this quality is decreased by bad administration conditions which are met in some hospitals or in ambulatory praxis. To eliminate these draw-backs and to ensure that theese medicaments to arrive the patients with a maximum of security, the unitary dose has been developped, particularly for oral liquid or solid forms, for drinkable liquids and for eye washings. For injectable medicaments the proposed solutions are still far from being satisfactory.

Injectable medicaments are generally provided in glass ampoules which have certains advantages for the manufactory, one of them being the low production cost. However their utilization is not free of inconveniences due to the fact that the ampoule is not in a form which is ready for its use. In this connection volume errors or calculations errors may be mentionned, as well as the possibility of incompatible mixtures in the same syringe, the contamination by particles or germs during the filling of the syringe (which is often reutilized), particular habits of the personnel of the hospital during the preparation and the later utilization of the medicaments, since in many hospitals the filling of the syringe is carried out long before the moment of injection. Finally the identification of the syringe is often missing or incorrect.

To eliminate this difficulties which may lead to serious accidents for patients, there is only one solution: the generalization of the unitary dose which alone permits the direct administration of an active principle without intermediate preparation.

Till now different types of unitary doses have been proposed in the form of self-injectable syringes or prefilled syringes.

The difficulties met therewith during their fabrication or their use have however not permitted their broad commercialisation.

Moreover the total cost stays a major obstacle to their generalization. Finally some of the proposed devices are not completely satisfactory because they require the piercing of a membrane or of a stopper by means of an expensive double needle, with risks of detaching solids particles of the membrane or of the stopper, which particles may enter into the liquid medicament and be injected therewith into the patient's tissue.

The device which resolves all of theese problems and which provides the closest prior art with respect to the present invention is described in the published european patent application Nr. No. 111 796 of the same applicant.

In this embodiment, the ampoule comprises a narrowed zone of relatively great axial dimensions. The stopper means is disposed within this narrowed zone during the whole storage time of the syringe. Because of this narrowed zone, the stopper means made of elastomeric materiel is strongly compressed during a storage time which may extend over several years, so that it may undergo a negative deformation, a kind of retentivity able to prevent a quick return back movement of said stopper means when the syringe is being used. This phenomenon risks to jeopardize the normal working of the stopper means and particulary of the peripheral rim arranged around the hollow cylindrical member of the stopper means which its disposed downstream of the radial channel. Even though the replacement of one rim by several annular lips being disposed one under the other, and a preliminary selection of the components may permit to overcome the mentioned inconveniences, there are much simpler solutions which are the subject of the present invention.

Moreover, in the system relating to the prior art the positioning of the stopper means creates a relatively high pression in the interior of the ampoule. In order to reduce this pression which is beneficial to be maintained on a relatively low level, their are several possibilities: a partial vacuum may be provided which is compensated at the moment of the positioning of the stopper means, or the stopper means may be introduced in compressed condition to let the gas escape, or by providing above the medicament to be injected a gas volume which is substantially twice the volume of the stopper means. Theese three solutions however are not very interesting, the first two of them because of the complexity and the cost of the installation, the third one because of the increased volume of the syringe.

Finally there is the problem of fabrication tolerances of the ampoule and the stopper means. Since the fabrication tolerances of the ampoule are in the order of $+/-0.15$ mm and those of the stopper means in the order of $+/-0.10$ mm, in certains extreme cases the compression at the level of the narrowed zone is excessive and the positioning of the stopper means is therefore getting difficult due to a strong friction of the peripheral rims which are arranged downstream of the radial channel, resulting in a difficult movement of the stopper means which acts like a piston within the body of the ampoule. A preliminary selection of the ampoules and the stopper means regarding to their cross section, their separation into batches of same dimensions, followed by appropriate marking may eventually be an acceptable solution to this problem. However, such a solution even though realisable may remain expensive.

The present invention aims to eliminate all these drawbacks of the prior art by extremely simple constructive means which avoid the necessity of expensive and complex installations.

Therefore the prefilled ampoule-syringe according to the invention is caracterized in that the peripheral rim provided downstream of the radial channel is disposed below the narrowed zone of the ampoule when the stopper means is in the storage position such that it is bound to only a weak compression during the storage.

According to a first embodiment, the narrowed zone may be adjacent to the open end of the ampoule, the peripheral rim being located in this case outside the ampoule when the stopper means is in the storage position.

According to a second embodiment, the narrowed zone may be located behind an enlarged belt adjacent to the open end of the ampoule, the peripheral rim being disposed in this case in said belt when the stopper means is in the storage position.

In the latter case, the neck of the ampoule is divided into two portions, one of which with reduced cross section provides an obturation zone during the storage and the other one, which was called enlarged belt, the diameter of which being essentially equal to the body of the ampoule permits positioning the rim or the rims or the tightness lips provided downstream from the opening of the radial channel, during the storage, thereby avoiding an excessive compression of the rim and theireby eliminating the risk of a permanent deformation. Since the cross section of the enlarged belt is essentially equal to that of the body of the ampoule, the flexible rim is bound to the same compression during the storage as during the injection. Consequently, its elastical caracteristics remain intact during the storage, which ensures its quasi instantaneous positioning after the increasing compression to which it is bound as it passes through the narrowed zone. The time during which this compression occurs is thereby substantially reduced and the rim of elastomeric material may thereby not suffer any permanent deformation which might endanger the efficiency of the system. In practice just as the compression occurs the operator keeps the meedle holding tip at top and presses against the ampoule. The rim provided beneath the opening of the radial channel passes beyond this narrowed zone by a single push during the preliminary air escape phase, that is before the needle of the syringe is pushed into the patient's tissue.

Since the effective height of said narrowed zone is reduced, the volume reduction of the gas located above the liquid medicament within the ampoule corresponds only to a fraction on the volume of the stopper means, which resolves the problem of the over-pressure due to the positioning of that stopper means, or of the dimensioning of the ampoule, the gas volume of which being consequently reduced.

Advantageously, as no negative deformation occurs according to a loss of elasticity of the elastomeric material during the storage, it is not necessary any more to compensate this deformation by exaggerating the dimensions of the rim or the tightening lips. This rim may therefore be fabricated in its exact dimensions and the syringe being stored for a month or several years has pratically no influence on the reaction speed of the rim or of the lips when the stopper means is brought into working position. Therefore a preliminary selection is no more necessary; thus the handling costs and consequently the manufacturing costs of these syringes may be reduced.

Another advantage of this conception results from the rim being a protrusion located beneath the opening of the radial channel and being situated during the storage beneath the narrowed zone, it constitutes thereby a retention means inhibiting the accidental compression of the stopper means which acts as a piston within the ampoule. This security is added to the very low over-pressure produced within the ampoule by the positioning of the stopper means, so that the piston has a tendency to be pushed out of the ampoule. To be pushed towards inside the body of the ampoule, the piston has to be deliberately pressed therein and preferably a small rotation of the ampoule with respect to the capsule may be carried out to facilitate the passing of the rim through the narrowed zone. As soon as this zone is passed, the compression of the rim within the ampoule is extremely weak and thus ensures a maximum flexibility during injection. This compression may however be calculated at its minimum since there is no danger of permanent deformation as explained above.

Moreover, since the radial channel is provided within a particularly soft elastomeric material, this channel get a reduced diameter or will be completely obstructed due to the compression of the stopper means when the pressure is too high. This phenomenon, which is in fact not an inconvenience, provides a self-regulation of the flow rate of the liquid medicament during the injection. By this conception the system imposes an essentially constant speed of injection and excludes an injection by fits and starts or a too rapid one.

The height of the stopper head of the stopper means may be lower or higher than the height of the narrowed zone of the ampoule. Thereby the manufacturing tolerances are not critical and the tightness of the syringe during the storage is assured in whatever position the head of the stopper means may be in respect to the surface of that narrowed zone, however under the condition that the opening of the radial channel be either at the level of that narrowed zone or beneath that zone.

According to a prefered embodiment of the invention, the diameter of the stopper head of the stopper means is greater than or equal to the diameter of the narrowed zone of the ampoule, but smaller than the inner diameter of the body of the ampoule, thereby ensuring the tightness of the ampoule when the stopper means is in the storage position and providing an annular space between the peripheral surface of said stopper head and the interior surface of the body of the ampoule when the stopper means is in its working position.

Since the stopper head must ensure a perfect tightness of the ampoule during the storage, its peripheral wall must be strongly pressed against the inner surface of the narrowed zone during the storage. To allow the medicament to flow during the injection, it is necessary that the stopper head has a diameter which is smaller than the inner diameter of the body of the ampoule.

To facilitate the passing of the annular rim through the narrowed zone, the enlarged belt adjacent to the open end of the ampoule has advantageously at least over a part of its height a conical surface the diameter of which varies from the value of the maximum inner diameter of said belt progressively to the diameter of the narrowed zone.

The outer surface of the ampoule adjacent to its open end comprises advantageously a protruding edge forming engagement means provided to cooperate with complementary engagement means integral with the capsule, wherein the capsule stopper means and the stiffening tip are preferably designed so that when said engagement means are engaged into each other the stopper head is compressed and abuts on the surface of the narrowed zone and the peripheral rim is slack or only under low compression within the enlarged belt of the ampoule. The precise positioning of those outer engagement means ensures a precise positioning of the inner members.

To ensure a sufficient flexibility of the stopper means, the stopper head and the hollow cylindrical member have preferably the shape of a hollow cup made of a soft elastomeric material, the walls of which have a cross section such that the length of the radial channel may not be greater than 5 mm.

The stiffening tip comprising an axial channel has preferably at its upper end an annular recess and a sectorial notch provided to bring its axial channel into communication with that annular recess. These constructive details allow a specially easy manufactoring of the stiffening tip whereas a sufficient communication between the radial channel and the axial channel of the stopper means are guaranteed.

Figure 2:
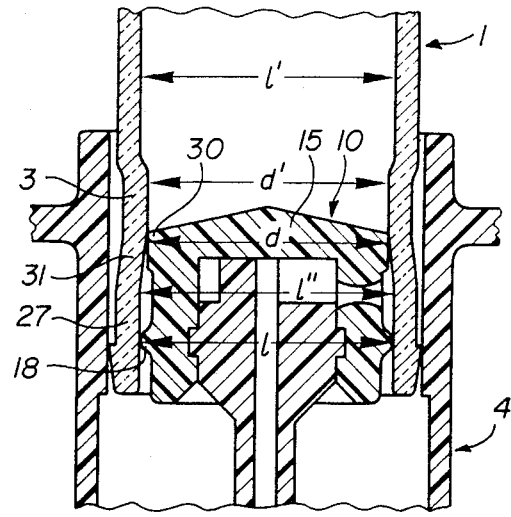
Figure 3:
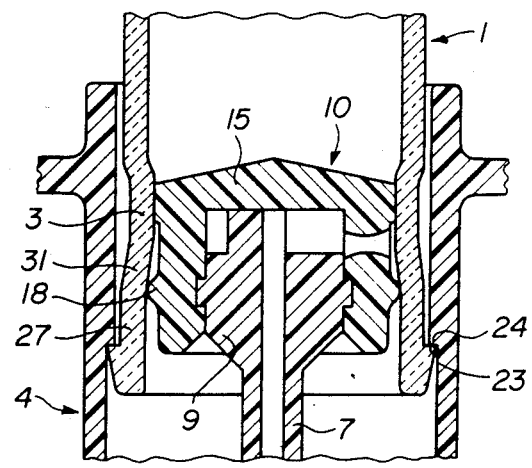

The present invention, its main advantages and its main features will be better understood with reference to the description of embodiments and the accompanying drawings, wherein:

FIG. 1 shows an axial section view of a prefered embodiment of a syringe according to the invention, FIG. 2 shows a partial section view of the syringe of FIG. 1, illustrating particularly the beginning of the phase of positioning the stopper means, FIG. 3 shows a view similar to that of FIG. 2, illustrating the position of the stopper means during the storage of the syringe, FIG. 4 is a view similar to those of FIGS. 2 and 3, illustrating an intermediary position of the stopper means between the storage and the working position, FIG. 5 is a view similar to that of FIGS. 2 and 4, illustrating the stopper means in working position, FIG. 6 shows an other embodiment of the stopper means which is in storage position, and FIG. 7 shows still another embodiment of the stopper means, also illustrated in storage position.

Refering to FIG. 1, the unitary dose syringe, which is shown in its storage position, comprises an ampoule 1 closed at one of its ends and provided with an opening 2 at its other end, further comprising a zone 3 of narrowed cross section with respect to its body, said zone being located adjacent to the open end 2. A hollow capsule 4 is arranged above the ampoule 1 and its open end 2. This capsule comprises a head 5, having preferably a continuous cylindrical sidewall, which may otherwise be only sectorial, and a bottom 6 which its connected to a central tubular member 7. A needle holding tip 8, which is also connected to the bottom 6 of the capsule 4, is aligned with the central tubular member 7 the upper end of which forms a stiffening tip 9 which carries the stopper means 10. This stopper means 10, as described in more details below, comprises two different functions. The first function is carried out during storage of the syringe and consists in providing the tightness of the ampoule containing a liquid medicament 12 and a gas pocket 13 which is arranged above the liquid, in the position of the syringe as shown in FIG. 1. The second function is carried out during the use of the syringe and consists in serving as a piston for pressing the medicament out through an axial channel 14 provided within the central tubular member 7 and the needle holding tip 8, in direction to a needle (not shown) which may be coupled to this tip by whatever means.

The stopper means 10 made of a flexible elastomerical material comprises an upper portion in the form of a stopper head 15 of substantially cylindrical shape and a hollow cylindrical member 16. This assembly is connected with the stiffening tip 9 on which the hollow cylindrical member 16 is fastened by means of retainers 17. The hollow cylindrical member 16 is provided with a peripheral rim 18, arranged next to its lower free end. A radial channel 19 is disposed across the hollow cylindrical member 16. This radial channel communicates with the axial channel 14 through an annular recess 20 and a sectorial notch 21 located in the upper end of the stiffening tip 9.

The two functions of the stopper means 10 are carried out respectively by the stopper head 15, the diameter of which is equal to or greater than the inner diameter of the narrowed zone 3 of the ampoule 1 to assure a perfect tightness of this ampoule during the storage of the liquid medicament 12, and by the peripheral rim 18 which serves as a piston ring during the injection phase, thus forcing the liquid medicament to penetrate into the radial channel 19 without escaping through the opening of the ampoule. The respective positions and their status for each phase of use of the syringe will be described in more details with reference to the following figures.

The capsule 4 is advantageouslyly equipped with a pair of wings 22 for easier manipulation of the syringe during the phase of injection. The open end 2 of the ampoule 1 preferably comprises a protruding edge 23 provided to cooperate with a projection 24 integral with the interior lateral surface of the head 5 of the capsule 4. These elements constitute retaining means by which an accidental ejection of the stopper means out of the ampoule due to the slight over-pressure in its interior may be avoided. A label formed for example by a banderole sticking simultaneously to the outer wall of the ampoule and to the edge 26 of the sidewall of the capsule 4 above the wings 22 guarantees the invulnerability of the syringe before its final utilization.

The embodiment illustrated in FIG. 1 shows an ampoule 1 in which the narrowed zone 3 is not directly adjacent to the open end 2, but it is separated from the latter by an enlarged belt 27 in which the peripheral rim 18 is embedded during the storage phase illustrated in that figure.

FIG. 2 illustrates the beginning of the positioning of the stopper means 10 and the capsule 4 coupled with said stopper means. The stopper head 15 has a diameter d equal to or preferably slightly higher than the inner diameter d' of the narrowed zone 3 of the ampoule. In the prefered embodiment shown in this figure the side edge 30 abuts against the upper end of a conical zone 31 of the ampoule, which forms the junction between the narrowed zone 3 and the enlarged belt 27 of the ampoule 1. At this stage the stopper head 15 is pratically subject to no compression other than just a small contracting force on the level of its side edge 30.

The diameter l of the peripheral rim 18 is at least equal to or preferably slightly higher than the diameter l' of the interior of the body of the ampoule 1. Actually, as mentioned above, the rim 18 serves as a piston ring when the stopper means is put in its working position, the piston ring thereby ensuring the tightness against the wall of the ampoule for preventing leakage of the liquid medicament through the opening of the ampoule. The enlarged belt 27 has preferably a diameter l'' equal to the diameter l' of the body of the ampoule. In this way the peripheral rim 18 is bound to a small compression during the storage phase, namely the same compression as the one to which it will be bound during the injection, so that all above mentioned problems of permanent deformation which may be provoqued by excessive compression of the rim during the storage phase are avoided. In order to completely eliminate this risk it would be sufficient providing a diameter 1″ of the belt 27 which is higher than the diameter 1 of the rim 18.

Upon continuing to thrust the capsule and the stopper means in the direction of the arrow A, a position as illustrated in the FIG. 3 is obtained. In this position the stopper head 15, whose height is in this case slightly smaller than the height of the narrowed zone 3 of the ampoule 1 such that pratically all risks of erroneous positioning due to accumulations of fabrication tolerances is eliminated, is completely engaged in this narrowed zone, whereby it is slightly if not strongly compressed in the interior of this zone. A strong compression does not prejudice the proper functioning of the system since the only function of this stopper is to assure the tightness of the ampoule during the storage phase. Consequently, if after a particulary long storage this stopper has lost more or less its elasticity and cannot immediately return to its slack state when the stopper means penetrate into the body of the ampoule, this does not constitute an inconvenience since the wall of the piston ring is maintained by the peripheral rim 18, for which precautions avoiding the phenomenoun of permanent deformation were taken. The position as illustrated in this figure corresponds to the storage of the syringe. The peripheral rim is located in the belt 27 of enlarged cross section or eventually in the largest portion of the conical zone 31 which forms the junction between the narrowed zone 3 and the belt 27 of enlarged cross section. The protruding exterior edge 23 of the ampoule is abutting against the projection 24 disposed at the interior of the sidewall of the capsule 4. Since the stopper means 10 is integral with the capsule 4, the precise positioning of the projecting elements 23 and 24 determines precisely the position of the stopper means 10 within the ampoule during the storage phase by means of the central tubular member 7 and the stiffening tip 9.

Upon passing from its position as in FIG. 2 to the position of FIG. 3, the stopper means creates in the interior of the ampoule a slight overpressure due to the decrease of the volume within said ampoule. This decrease of the volume is equal to the product of the cross section of the ampoule in the narrowed zone into the stroke of the stopper means between both positions. If this pressure, which represents certain advantages as far as the protection of the medicament contained in the ampoule against accidentially contamination is concerned, should be reduced, one could effect a filling with the partial vacuum such that the increase of pressure be partially set off by the partial vacuum provided during the filling operation.

FIG. 4 illustrates the preparatory phase of the syringe before the injection. During this phase the operator pushes against the ampoule in the direction of arrow B, whereby care has to be taken for directing the syringe upwards so that the gas which was initially contained in the ampoule may escape. This phase consists of passing the peripheral rim 18 over the narrowed zone 3, thus binding the rim to a relatively high compression force but of short duration. The stopper head 15 has now passed behind the narrowed zone 3 and may expand freely. Its diameter d is smaller than the diameter 1′ of the body of the ampoule 1 such that an annular space 40 is provided between the side portion of the stopper head the inner wall of the body of the ampoule and allows the liquid medicament to flow towards the radial channel 19.

The passing of the peripheral rim 18 from the position illustrated in FIG. 3 to the one illustrated in FIG. 4 constitutes an intermediary step between a first position, in which the annular rim 18 acts as an essentially passive retention means which avoids an accidental movement of the ampoule in the direction of arrow B in respect to the capsule, and a second position in which it plays an active part as a piston ring as further illustrated in FIG. 5.

FIG. 5 illustrates the syringe in its working position. The movement of the ampoule 1 in the direction of arrow C in respect to the capsule 4 and to the stopper means 10 connected to said capsule achieves the evacuation of the liquid medicament in the direction of arrow F through the radial channel 19, the sectional groove 21 arranged in the stiffening tip 9 and the axial channel 14 of the central tubular element 7. The annular rim 18, upon rubbing against the inner wall of the body of the ampoule, plays the role of a piston ring and forces the liquid to follow the described way. Since the rim 18, which may however be replaced by a plurality of parallel lips, is disposed immediately under the outer opening of the radial channel 19, the dead volume that is the quantity of medicament remaining in the syringe after the injection may be reduce to a minimun.

FIG. 6 illustrates a modified form in which the height of a cylindrical surface 60 extending laterally around the stopper head 15 and around the upper portion of the hollow cylindrical member 16 is greater than the height of the narrowed zone 3 of the ampoule. This solution may be of interest in order to avoid that the positioning of the stopper means with respect to the narrowed zone 3 may be carried out with problems with respect to tolerance.

The embodiment illustrated in FIG. 7 differs from the preceding embodiments in that the narrowed zone 3 is adjacent to the open end of the ampoule. In this case the peripheral rim 18 may be located outside the ampoule during the storage phase, whereby it may not be bound to any compressive force during that phase, while maintaining its role of retention means for avoiding an accidental penetration of the stopper means into the ampoule.

The concrete embodiment illustrated in this figure shows the separation of the functions of the stopper means and of the annular peripheral rim. With respect to an ampoule the body of which has an inner diameter of 10.00 mm, the inner diameter of the narrowed zone should be 9.00 mm, the diameter of the stopper head should be between 9.20 and 9.80 mm, and the diameter of the rim may be for example 10.25 mm.

During the injection phase, the stopper head is within the body of the ampoule. The mean width between the inner surface of the ampoule and the peripheral surface of the stopper head may be between 0.10 and 0.40 mm. With respect to the first of these values the outflow of the medicament occurs normally and the dead volume, that is the quantity of the medicament which will be left in the ampoule after the injection is very small. For the second value the outflow of the medicament is very good but the dead volume is larger.

During the storage the stopper head is within the narrowed zone. The difference of the diameters of the narrowed zone and of the stopper head may be between 0.20 and 0.80 mm. This difference must be absorbed by the compression of the stopper head. The stronger the compression is, the better is the tightness of the ampoule during the storage but the greater is the resistance against the detachment at the beginning of the utilization of the syringe.

According to above the dimensions of the narrowed zone and of the rim, the compression of said rim, that is the reduction of its diameter at the moment the stopper head passes from its storage position to its working position, is approximately 1.25 mm. In practice it was established that a reduction of 1.75 mm due for instance to an underdementioned diameter of the narrowed zone, may cause a jamming of the system.

A contraction of 0.25 mm of this rim, when the rim is within the ampoule and acts as a piston ring, is sufficient to avoid parasitic outflow of the medicament towards the opening of the ampoule.

In practice, the diameter of the stopper head must be at least 0.10 mm. smaller than the inner diameter of the body of the ampoule and 0.10 mm greater than the diameter of the narrowed zone. The diameter of the peripheral rim must be at least 0.10 mm greater than the inner diameter of the body of the ampoule.

A solution to avoid possible problems of bad functioning may consist in eliminating the tolerance by appropriate selection of the components. In this case the diameter of the body of the ampoule may be fixed at 10.00 mm, the one of the stopper head at 9.90 mm, the one of the narrowed zone of the ampoule at 9.80 mm and the one of the rim at 10.10 mm. The compression of the stopper head during storage is 0.10 mm, that of the rim during operation equally 0.10 mm. and the mean width of the annular space permitting the outflow of the liquid is 0.05 mm.

Taking into account the tolerances, the inner diameter of the body of the ampoule is 10+/−0.50 mm, the one of the stopper head 9.65+/−0.10 mm, the one of the narrowed zone of the ampoule 9.35+/−0.10 mm and the one of the rim is 10.35+/−0.10 mm.

The compression of the stopper head during the storage, the compression of the rim during operation and the mean width of the annular space are comprised respectively between 0.1 and 0.5 mm, 0.1 and 0.6 mm, and 0.05 and 0.30 mm.

Another remarkable advantage of the syringes described thereinbefore is the presence of a slight overpressure in the ampoule. In practice, with the dimensions as described above, the level of the liquid is proposed to be maintained approximatively 5 mm under the stopper means during the storage. A greater distance would eliminate the advantage of the over-pressure and increase the size of the device. The overpressure depend on the reduction of the compressed volume during the positioning of the stopper. The movement of the stopper means depend on the height of the narrowed zone and on the initial position of the radial channel. The reduction of the volume is proportional to the stroke of the stopper means between its storage position and the beginning of the working position. In theory, the height of gas may be determined such that the gas has attained its limit for compression at the end of the stroke of the stopper means. However this would cause the jamming of the system by deformation of the stopper means.

The height of the gas above the medicament during the storage is determined such that the operator may easily put the stopper means in an intermediate position between the storage position and the working position, in which the radial channel opens into the body of the ampoule, in which the rim is situated such that its function as piston ring is ensured and in which the medicament surrounds the stopper head and the opening of the radial channel.

This is an ideal position because it allows a correct positioning of the annular rim after its passing through the narrowed zone.

If the height of gas is insufficient, the liquid risks touching the annular rim before the latter is correctly situated. To avoid the risks of leakage, the rim may be reinforced or provided in double for instance in the form of two superposed annular strips.

In practice, the height of gas is provided with 8.00 mm before the stopper means is put in place. This positioning creates a height reduction of 3.00 mm. During storage the height of gas is 5 mm and the pressure is in the order of 1.6 bar. In order to bring the stopper means into a position in which the gas may escape, the necessary movement of the stopper is in the order of 2 mm, such that the pressure of the gas immediately before escaping from the syringe attains 2.6 bar. A final movement in the order of 1 mm brings the liquid into the ideal position as mentioned above.

The above values are given as examples and not as limitations, while the described syringe may undergo various modifications which are obvious to the man skilled in the art, without leaving the scope of the present invention.

We claim:

1. A prefilled ampoule-syringe of unitary dose comprising an ampoule open at one of its ends and having a narrowed zone near said end, stopper means of elastomeric material engaged within the ampoule and axially movable between a storage position and a working position, the stopper means having an interior conduit provided for bringing into communication a needle holding tip and the interior of the ampoule when the stopper means is in its working position, the interior conduit comprising an axial channel and a radial channel connected to the axial channel, the stopper means being secured to a capsule arranged around the zone of the open end of the ampoule, said stopper means comprising a stopper head which is prolonged by a flexible hollow cylindrical member which covers a central stiffening tip connecting the stopper means and the capsule, said hollow cylindrical member including said radial channel and at least one peripheral rim provided downstream from the radial channel, wherein the peripheral rim provided downstream from the radial channel is disposed below said narrowed zone of the ampoule when the stopper means is in said storage position, so that it is subjected to only a weak compression during storage.

2. The ampoule-syringe of claim 1, wherein the narrowed zone is adjacent to the open end of the ampoule, and the peripheral rim is located outside the ampoule when the stopper means is in said storage position.

3. The ampoule-syringe of claim 1, wherein the narrowed zone is located behind an enlarged belt adjacent to said open end of the ampoule, and the peripheral rim is located within said belt when the stopper means is in said storage position.

4. The ampoule-syringe of claim 1, wherein the height of the stopper head of the stopper means is less than the height of the narrowed zone of the ampoule.

5. The ampoule-syringe of claim 1, wherein the height of the stopper head of the stopper means is greater than the height of the narrowed zone of the ampoule.

6. The ampoule-syringe of claim 1, wherein the diameter of the stopper head of the stopper means is greater than or equal to the diameter of the narrowed zone of the ampoule, but smaller than the inner diameter of the body of the ampoule, such that the tightness of the ampoule is ensured when the stopper means is in the storage position, and an annular space is provided between the peripheral surface of said stopper head and the inner surface of the body of the ampoule when the stopper means is in its working position.

7. The ampoule-syringe of claim 3, wherein the enlarged belt comprises at least over a part of its height a conical zone the inner diameter of which varies from the maximum inner diameter of said belt progressively to the diameter of the narrowed zone.

8. The ampoule-syringe of claim 1, wherein the outer surface of the ampoule comprises a protruding edge adjacent to the open end thereof, forming engagement means for cooperating with complementary engagement means integral with the capsule, wherein the stopper means and the stiffening means are designed so that the stopper head abuts at least partially on the inner surface of the narrowed zone and the peripheral rim is slack or only under low compression when said respective engagement means are engaged with each other.

9. The ampoule-syringe of claim 1, wherein the radial channel has a length not greater than 5.00 mm.

10. The ampoule-syringe of claim 1, wherein the stiffening tip comprises an axial channel, an annular recess at its upper end and at least one sectorial notch provided to bring into communication said axial channel and said annular recess.

* * * * *